US010111882B2

(12) United States Patent
Abella et al.

(10) Patent No.: US 10,111,882 B2
(45) Date of Patent: Oct. 30, 2018

(54) SYK INHIBITORS

(71) Applicant: Gilead Sciences, Inc., Foster City, CA (US)

(72) Inventors: Esteban M. Abella, Emerald Hills, CA (US); Julie A. Di Paolo, San Francisco, CA (US); Kathleen S. Keegan, Bainbridge Island, WA (US); Antonio Mario Querido Marcondes, Millbrae, CA (US); Yang Pan, San Mateo, CA (US); Arati V. Rao, Palo Alto, CA (US)

(73) Assignee: GILEAD SCIENCES, INC., Foster City, CA (US)

(*) Notice: Subject to any disclaimer, the term of this patent is extended or adjusted under 35 U.S.C. 154(b) by 0 days.

(21) Appl. No.: 15/705,139

(22) Filed: Sep. 14, 2017

(65) Prior Publication Data

US 2018/0071302 A1    Mar. 15, 2018

Related U.S. Application Data (60) Provisional application No. 62/429,209, filed on Dec. 2, 2016, provisional application No. 62/416,047, filed on Nov. 1, 2016, provisional application No. 62/394,573, filed on Sep. 14, 2016.

(51) Int. Cl.
   *A61K 31/535*    (2006.01)
   *A61K 31/5377*   (2006.01)
   *A61K 31/4985*   (2006.01)

(52) U.S. Cl.
   CPC ...... *A61K 31/5377* (2013.01); *A61K 31/4985* (2013.01)

(58) Field of Classification Search
   None
   See application file for complete search history.

(56) References Cited

U.S. PATENT DOCUMENTS

| | | | |
|---|---|---|---|
| 3,845,770 A | 11/1974 | Theeuwes et al. |
| 4,326,525 A | 4/1982 | Swanson et al. |
| 4,902,514 A | 2/1990 | Barclay et al. |
| 4,992,445 A | 2/1991 | Lawter et al. |
| 5,001,139 A | 3/1991 | Lawter et al. |
| 5,023,252 A | 6/1991 | Hseih |
| 5,035,878 A | 7/1991 | Borch et al. |
| 5,616,345 A | 4/1997 | Geoghegan et al. |
| 6,121,419 A | 9/2000 | Rowley et al. |
| 7,338,938 B2 | 3/2008 | Rodgers et al. |
| 7,435,814 B2 | 10/2008 | Singh et al. |
| 8,227,455 B2 | 7/2012 | Masuda et al. |
| 8,299,056 B2 | 10/2012 | Bahmanyar et al. |
| 8,440,667 B2 | 5/2013 | Mitchell et al. |
| 8,440,689 B2 | 5/2013 | Arikawa et al. |
| 8,450,321 B2 | 5/2013 | Mitchell et al. |
| 8,455,493 B2 | 6/2013 | Mitchell et al. |
| 8,470,835 B2 | 6/2013 | Atkinson et al. |
| 8,748,607 B2 | 6/2014 | Mitchell et al. |
| 8,765,761 B2 | 7/2014 | Mitchell et al. |
| 8,796,270 B2 | 8/2014 | Mitchell |
| 8,962,835 B2 | 2/2015 | Mitchell et al. |
| 9,120,811 B2 | 9/2015 | Mitchell et al. |
| 9,212,191 B2 | 12/2015 | Mitchell et al. |
| 9,290,490 B2 | 3/2016 | Altman et al. |
| 9,290,505 B2 | 3/2016 | Blomgren et al. |
| 9,334,278 B2 | 5/2016 | Hermann et al. |
| 9,353,066 B2 | 5/2016 | Haidle et al. |
| 9,359,375 B2 | 6/2016 | Jia et al. |
| 9,376,418 B2 | 6/2016 | Haidle et al. |
| 9,376,441 B2 | 6/2016 | Currie et al. |
| 9,382,256 B2 | 7/2016 | Casteel et al. |
| 9,416,111 B2 | 8/2016 | Haidle et al. |
| 9,504,684 B2 | 11/2016 | Blomgren et al. |
| 9,562,056 B2 | 2/2017 | Blomgren et al. |
| 9,567,348 B2 | 2/2017 | Mitchell et al. |
| 9,657,023 B2 | 5/2017 | Elford et al. |
| 9,663,526 B2 | 5/2017 | Fensome et al. |
| 9,687,492 B2 | 6/2017 | Di Paolo et al. |
| 9,707,236 B2 | 7/2017 | Di Paolo et al. |
| 9,796,718 B2 | 10/2017 | Mitchell et al. |
| 9,827,309 B2 | 11/2017 | Strack et al. |
| 9,868,716 B2 | 1/2018 | Xu et al. |
| 9,918,939 B2 | 3/2018 | Casteel et al. |
| 9,931,338 B2 | 4/2018 | Blomgren et al. |
| 9,949,932 B2 | 4/2018 | Casteel et al. |

(Continued)

FOREIGN PATENT DOCUMENTS

| | | |
|---|---|---|
| WO | WO-2009/029682 | 3/2009 |
| WO | WO-2011/014515 | 2/2011 |

(Continued)

OTHER PUBLICATIONS

Currie et al., "Discovery of GS-9973, a Selective and Orally Efficacious Inhibitor of Spleen Tyrosine Kinase," Journal of Medicinal Chemistry, 2014, 57, 3856-3873.*
Walsh et al., "Proton pump inhibitors for the treatment of cancer in companion animals," Journal of Experimental & Clinical Cancer Research, 34:93 (published online Sep. 4, 2015).*
Abramson et al., "Advances in the biology and therapy of diffuse large B-cell lymphoma: moving toward a molecularly targeted approach." Blood 2005, 106(4), pp. 1164-1174.
Biomodels, Myelosupression, http://www.biomodels.com/disease-areas/cancer-supportive-care/myelosupression. (printed on Mar. 8, 2018).
Carey, PJ, "Drug-induced myelosuppression: diagnosis and management." Drug Safety, 2003, pp. 691-706. Abstract.
Cheson et al., "Monoclonal antibody therapy for B-cell non-Hodgkin's lymphoma." The New England Journal of Medicine, 2008, 359(6), pp. 613-626. (1 page).
Morton et al., "Lymphoma incidence patterns by WHO subtype in the United States, 1992-2001." Blood 2006, 107(1), pp. 265-276.

(Continued)

*Primary Examiner* — Jared Barsky
(74) *Attorney, Agent, or Firm* — Sheppard Mullin Richter & Hampton LLP (57) ABSTRACT

The application provides methods of treating or reducing thrombocytopenia, leukopenia, anemia, or neutropenia in a patient in need thereof, comprising the step of administering an effective amount of a compound selected from Compounds 1-6, disclosed herein.

6 Claims, 7 Drawing Sheets

(56) References Cited

U.S. PATENT DOCUMENTS

| | | | |
|---|---|---|---|
| 9,968,601 B2 | 5/2018 | Blomgren et al. | |
| 9,974,792 B2 | 5/2018 | Di Paolo et al. | |
| 2005/0232969 A1* | 10/2005 | Andre | A61K 31/473 424/423 |
| 2006/0276459 A1 | 12/2006 | Masuda et al. | |
| 2010/0009364 A1 | 1/2010 | Fantl et al. | |
| 2010/0152159 A1 | 6/2010 | Mitchell et al. | |
| 2010/0222323 A1 | 9/2010 | Mitchell et al. | |
| 2011/0152273 A1 | 6/2011 | Arikawa et al. | |
| 2012/0220582 A1 | 8/2012 | Mitchell et al. | |
| 2013/0210802 A1 | 8/2013 | Blomgren et al. | |
| 2013/0231330 A1 | 9/2013 | Mitchell et al. | |
| 2013/0237520 A1 | 9/2013 | Mitchell et al. | |
| 2013/0237521 A1 | 9/2013 | Mitchell et al. | |
| 2013/0267496 A1 | 10/2013 | Mitchell et al. | |
| 2013/0310363 A1 | 11/2013 | Mitchell et al. | |
| 2014/0148430 A1 | 5/2014 | Blomgren et al. | |
| 2014/0336169 A1 | 11/2014 | Mitchell et al. | |
| 2014/0357627 A1 | 12/2014 | Mitchell et al. | |
| 2015/0038488 A1 | 2/2015 | Currie et al. | |
| 2015/0038492 A1 | 2/2015 | Jia et al. | |
| 2015/0038504 A1 | 2/2015 | Casteel et al. | |
| 2015/0038505 A1 | 2/2015 | Elford et al. | |
| 2015/0150881 A1 | 6/2015 | Di Paolo et al. | |
| 2015/0175616 A1 | 6/2015 | Blomgren et al. | |
| 2015/0266902 A1 | 9/2015 | Blomgren et al. | |
| 2015/0290171 A1* | 10/2015 | Adams | A61K 38/29 424/142.1 |
| 2015/0307491 A1 | 10/2015 | Su et al. | |
| 2016/0002221 A1 | 1/2016 | Su et al. | |
| 2016/0031894 A1 | 2/2016 | Mitchell et al. | |
| 2016/0045508 A1 | 2/2016 | Vazquez et al. | |
| 2016/0052930 A1 | 2/2016 | Fensome et al. | |
| 2016/0058758 A1 | 3/2016 | Blomgren et al. | |
| 2016/0130659 A1 | 5/2016 | MacIsaac et al. | |
| 2016/0166579 A1 | 6/2016 | Di Paolo et al. | |
| 2016/0166580 A1 | 6/2016 | Casteel et al. | |
| 2016/0168155 A1 | 6/2016 | Fung et al. | |
| 2016/0185744 A1 | 6/2016 | Xu et al. | |
| 2016/0193334 A1 | 7/2016 | Strack et al. | |
| 2016/0220573 A1 | 8/2016 | Di Paolo et al. | |
| 2016/0310490 A1 | 10/2016 | Blomgren et al. | |
| 2016/0368918 A1 | 12/2016 | Blomgren et al. | |
| 2016/0375019 A1 | 12/2016 | Di Paolo et al. | |
| 2017/0020821 A1 | 1/2017 | Casteel et al. | |
| 2017/0035755 A1 | 2/2017 | Blomgren et al. | |
| 2017/0095490 A1 | 4/2017 | Blomgren et al. | |
| 2017/0121350 A1 | 5/2017 | Blomgren et al. | |
| 2017/0173034 A1 | 6/2017 | Di Paolo | |
| 2017/0217967 A1 | 8/2017 | Elford et al. | |
| 2017/0258804 A1 | 9/2017 | Di Paolo et al. | |
| 2018/0008608 A1 | 1/2018 | Di Paolo et al. | |
| 2018/0071303 A1 | 3/2018 | Abella et al. | |
| 2018/0086769 A1 | 3/2018 | Armistead et al. | |
| 2018/0099971 A1 | 4/2018 | Elford et al. | |
| 2018/0117052 A1 | 5/2018 | Di Paolo et al. | |

FOREIGN PATENT DOCUMENTS

| | | |
|---|---|---|
| WO | WO-2015/100217 | 7/2015 |
| WO | WO-2016/010809 | 1/2016 |

OTHER PUBLICATIONS

Schoch et al., "AML with 11q23/MLL abnormalities as defined by the WHO classification: incidence, partner chromosomes, FAB subtype, age distribution, and prognostic impact in an unselected series of 1897 cytogenetically analyzed AML cases." Blood, 2003, 102, pp. 2395-2402.

Wierda, W.G., "Current and Investigational Therapies for Patients with CLL." Hematology 2006, pp. 285-294.

Basecke et al., "The MLL partial tandem duplication in acute myeloid leukaemia." 2006, British Journal of Haematology, 135, 438-449.

Chang et al., "Spleen tyrosine kinase mediates the actions of EPO and GM-CSF and coordinates with TGF-ß in erythropoiesis." Biochemica et Biophysica Acta 1864, (2017), 687-696.

Collins et al., "Deregulation of the HOXA9/MEIS1 Axis in Acute Leukemia." Curr Opin Hematol. Jul. 2016 ; 23(4): 354-361.

Crow et al., "Inhibition of Immune Thrombocytopenic Purpura (ITP) by an Orally Bioavailable Inhibitor of SYK Kinase Activity." Blood 2005; 106:2165. Abstract.

Hofmann et al., "Myelodysplastic Syndrome." Annu. Rev. Med. 2005, 56: pp. 1-16.

International Search Report and Written Opinion for International Application No. PCT/US2017/051649 dated Jan. 30, 2018. (25 pages).

NCT02076412, "A Efficacy and Safety Study of Fostamatinib in the Treatment of Persistent/Chronic Immune Thrombocytopenic Purpura (ITP) (FIT)." ClinicalTrials.gov; Last Update Posted: Aug. 22, 2017.

NCT02343939 ("NCT"), Entospletinib Monotherapy and in Combination With Chemotherapy in Adults With Acute Myeloid Leukemia (AML) (ENTO in AML), (first submitted Jan. 16, 2015, first posted Jan. 22, 2015).

Nijjar et al., "Inhibition of spleen tyrosine kinase in the treatment of rheumatoid arthritis." Rheumatology 2013;52:1556-1562.

Non-Final Office Action for U.S. Appl. No. 15/705,159 dated Nov. 24, 2017. (13 pages).

Reilly et al., "PRT-060318, a novel Syk inhibitor, prevents heparin-induced thrombocytopenia and thrombosis in a transgenic mouse model." Blood, 2011, pp. 2241-2246.

Sharman et al., "Phase 2 Trial of Entospletinib (GS-9973), a Selective SYK Inhibitor, in Follicular Lymphoma (FL)", Blood 2014; 124:4419. Abstract.

Sitwala et al.,"HOX Proteins and Leukemia." Int J Clin Exp Pathol (2008) 1, 461-474.

Thorsteinsdottir et al., "NUP98—HOXA9 expression in hemopoietic stem cells induces chronic and acute myeloid leukemias in mice." The EMBO J. 2001; 20(3): pp. 350-361.

Final Office Action for U.S. Appl. No. 15/705,159 dated Jun. 18, 2018. (13 pages).

Friedberg et al., "Inhibition of Syk with fostamatinib disodium has significant clinical activity in non-Hodgkin lymphoma and chronic lymphocytic leukemia", Blood, 2010, vol. 115, No. 13, pp. 2578-2585.

Halaven, Adverse Events Grading Card, 2016. (8 pages).

International Search Report and Written Opinion for International Application No. PCT/US2017/051648 dated Mar. 9, 2018. (21 pages).

Sekhon et al., "Thrombocytopenia in Adults: A Practical Approach to Evaluation and Management", Southern Medical Journal, 2006, vol. 99, No. 5, pp. 491-498.

Uckun et al., "Liposomal Nanoparticles of a Spleen Tyrosine Kinase P-Site Inhibitor Amplify the Potency of Low Dose Total Body Irradiation Against Aggressive B-Precursor Leukemia and Yield Superior Survival Outcomes in Mice", EBioMedicine, 2015, 2, pp. 554-562.

Walker et al., "Interim Results of a Phase 1 b/2 Study of Entospletinib (GS-9973) Monotherapy and in Combination with Chemotherapy in Patients with Acute Myeloid Leukemia", Blood, 2016, 128:2831, Abstract. (6 pages).

* cited by examiner

SYK INHIBITORS

CROSS-REFERENCE TO RELATED APPLICATIONS

This application claims the benefit under 35 U.S.C. § 119(e) of United States Provisional Application Nos. 62/394,573, filed Sep. 14, 2016, 62/416,047, filed Nov. 1, 2016; and 62/429,209, filed Dec. 2, 2016, which are hereby incorporated by reference in their entirety.

FIELD

The present disclosure relates to methods of treatment of diseases and disorders using compounds and compositions that inhibit Spleen Tyrosine Kinase (SYK) activity.

BACKGROUND

Protein kinases, the largest family of human enzymes, encompass well over 500 proteins. Spleen Tyrosine Kinase (SYK) is a member of the family of tyrosine kinases, and is a regulator of early B-cell development as well as mature B-cell activation, signaling, and survival. SYK has roles in immunoreceptor- and integrin-mediated signaling in a variety of cell types, including B-cells, macrophages, monocytes, mast cells, eosinophils, basophils, neutrophils, dendritic cells, T-cells, natural killer cells, platelets, and osteoclasts. The inhibition of Syk activity can be useful for the treatment cancers and inflammatory diseases. U.S. Pat. Nos. 8,455,493, 8,440,667, 9,376,441, 9,416,111, 9,353,066 and 9,376,418 disclose SYK inhibitors. Several SYK inhibitors are in advanced stages of clinical trials. Fostamatinib is a SYK inhibitor currently undergoing phase III clinical trials for chronic immune thrombocytopenic purpura (chronic ITP). (NCT02076412; Clinicaltrials.gov). Fostamatinib, however, has adverse side effects including hypertension, neutropenia and transaminitis. (Nijjar J. S., et al., *Rheumatology* 2013, 1556-1562).

SUMMARY

Some embodiments provide methods for treating or reducing thrombocytopenia, leukopenia, anemia, or neutropenia in a patient in need thereof, comprising the step of administering an effective amount of a compound selected from:

Compound-1

Compound-2

Compound-3

Compound-4 and

Compound-5 or a pharmaceutically acceptable salt, ester or derivative thereof. Some embodiments provide methods of treatment for anemia, thrombocytopenia, leukopenia or neutropenia wherein said patient is not undergoing chemotherapy.

Some embodiments provide methods for treating a disease or condition selected from the group consisting of an inflammatory disorder, an allergic disorder, an autoimmune disease, and a cancer in a subject in need thereof, the method comprising administering to the human in need thereof a therapeutically effective amount of a compound selected from Compounds 1-6, or a pharmaceutically acceptable salt, ester or derivative thereof, wherein said subject is additionally undergoing proton pump inhibitor therapy; and, wherein said compound selected from Compounds 1-6 is administered at a daily dosage of about 25% to about 75% higher than the daily dosage recommended for a subject not undergoing proton pump inhibitor therapy.

Some embodiments provide methods for treating a proliferative disease or disorder in a subject in need thereof, comprising the step of administering a therapeutically effective amount of a compound selected from Compounds 1-6, or a pharmaceutically acceptable salt thereof, to said subject, wherein said subject has one or more abnormal core-binding karyotypes selected from t(8;21)(q22;q22), inv(16) (p13.1q22) and t(16;16)(p13.1;q22); or wherein said subject has one or more chromosomal abnormalities selected from the deletion of 5, 5q, 7, 7q, 17p, inv(3)(q21;q26) and t(3;3)(q21;q26); or wherein said subject has a 11q23 rearrangement of MLL gene.

Some embodiments provide methods for treating a proliferative disease or disorder in a subject in need thereof, comprising the step of administering a therapeutically effective amount of a compound selected from Compounds 1-6, or a pharmaceutically acceptable salt thereof, to said subject, wherein said subject has mixed lineage leukaemia gene-partial tandem duplications (MLL-PTD). MLL-PTD confer a worse prognosis with shortened overall and event free survival in childhood and adult AML. (Basecke J., et al., *British Journal of Hematology*, 2006, 135(4)).

Some embodiments provide methods for treating a proliferative disease or disorder in a subject in need thereof, comprising the step of administering a therapeutically effective amount of a compound selected from Compounds 1-6, or a pharmaceutically acceptable salt thereof, to said subject, wherein said subject has or expresses a mixed lineage leukemia (MLL) fusion protein, a BCR-ABL fusion protein, FLT3 internal tandem duplications, NPM1 mutation, IDH1 mutation, IDH2 mutation, a deleted or mutated p53, high or elevated levels of meningioma 1, and/or high or levels of lactate dehydrogenase. MLL fusion partners can vary and more than 51 fusion partners have been identified. MLL/AF9 often results in AML while MLL/AF4 oftent results in B-lineage ALL. (Basecke J. et al, supra.). Some embodiments provide methods for identifying abnormal MLL fusion protein expression in a patient followed by the administration of a compound selected from Compounds 1-6, or a pharmaceutically acceptable salt thereof to a patient in need thereof.

Homeobox (HOX) proteins are homeo-domain DNA binding transcription factors that play an important role in regulation of hematopoiesis (Sitwala, *Int. J. Clin. Exp. Pathol.* 2008, March 30; 1(6):461-74). Myeloid Ecotropic Viral Integration Site 1 (MEIS1) is a co-factor of Homeobox A9 (HOXA9) that recruits additional DNA binding proteins to HOXA9 binding sites in order to maintain the Mixed Lineage Leukemia (MLL) stem cell transcriptional program (Collins, *Curr. Opin. Hematol.* 2016, July; 23(4):354-61). Overexpression of these two proteins in hematopoietic stem cells (HSCs) results in a rapid and fatal leukemia when transduced HSCs are transplanted in mice (Thorsteinsdottir, *EMBO J.* 2001, February 1; 20(3):350-61). A subset of acute lymphoid leukemia (ALL), pro-B-acute lymphocytic leukemia (pro-B ALL), myelodysplastic syndrome (MDS) and T-ALL patients can be characterized by tumor cells collected from bone marrow showing high co-expression of HOXA9 and MEIS1 that are associated with increased SYK protein levels. Some embodiments provide a method for treating patients with ALL, pro-B ALL, MDS, AML, MDS and T-ALL where HOXA9 and MEIS1 are overexpressed by the administration of a therapeutically effective amount of a SYK inhibitor selected from Compounds 1-6, or a pharmaceutically acceptable salt, ester or derivative thereof.

Some embodiments provide methods for treating a proliferative disease or disorder in a subject in need thereof, comprising the step of administering a therapeutically effective amount of a compound selected from Compounds 1-6, or a pharmaceutically acceptable salt thereof, to said subject, wherein said subject is administered one or more anti-cancer agents selected from the group consisting of AMG-330, anti-miR155, AntiJL-1+, CD117-MTX aptamer, CD47mAb, CD-98mAb, GO-203c, hBF4-mAb, LAIR1-mAb, IL-IRAP-mAb, MG006, miR-150, MRX-6313, MSK-777, SP-2065, SPM-2, SIRPαFc, TTT-3002, MLL/Menin inhibitor, AML-IL2/CD80, 4G8SDIEM, AG-221, AG-120, AKN-028, ALT 801, Anti-CD44 mAb, ASP-2215, AT-109, AT-406, AT-9283, AZ-1208, BGB-324, BI 836858, BMS-936564, BP-100-01, Carbozatinib, CB-839, CART-CD123, CART-CD33, CPI-613, CPI-0610, CSL-362, CWP-232291, Dacogen, Dinacilib, DC/AML fusion, Elesclomol, EPZ-5676, GSK2879552, IGN 523, INNO-305, Iomab-B, KX-2391, LeY, LOR-253, MK-8242, MGD006, Oxi-4503, PF-449913, Plerixafor, PRI-724, Rebistanib, Rigosertib, RO-5503781, PF-04449913, SG-2000, SL-401, SGN-CD33a, TCN-P, Tiecycline, Triciribine, Vismodegib, Zosuquidar, Actimab-A, AEG 35156, Belinostat, B1811283, Bismab-A, Birinapant, BL-8040, CC-486, CNDO-109, Crenolanib, Deformolus, DFP-10917, Flavopiridol, GVAX, KB-004, KPT-330, Lestartinib, Lirilumab, LO-02040, LY209314, MK8776, Omacetaxine, Pacritinib, Panobinostat, PD-616, Pdilizumab, PR-104, Pracinostat, PLX-3397, R-115777, Ribovarin, Selumetinib, SGI-110, Sorafenib, Tresosulfan, Temodar, Tosedostat, Vorinostat, WT-1, Arsenix trioxide, Clofarabine, Decitabine, Laromustine, Tipfarnib, Palbocyclib, Quizartinib and Mylotarg.

DETAILED DESCRIPTION

Some embodiments provide methods for treating or reducing thrombocytopenia, leukopenia, anemia, or neutropenia in a patient in need thereof, comprising the step of administering an effective amount of a compound selected from:

Compound-1

Compound-2

Compound-3

Compound-4 and

Compound-5 or a pharmaceutically acceptable salt, ester or derivative thereof. Some embodiments provide methods of treatment for anemia, thrombocytopenia, leukopenia or neutropenia wherein said patient is not undergoing chemotherapy.

Without being bound to a mechanism or theory, the disclosure herein provides methods to increase neutrophil and platelet levels in patients in need thereof. It is the expectation that the compounds herein will be useful in the treatment of, for example, conditions that cause or exacerbate neutropenia, anemia, leukopenia and thrombocytopenia.

Some embodiments provide methods for treating anemia comprising the step of administering a therapeutically effective amount of a compound selected from Compounds 1-6 to a subject in need thereof. In some embodiments, anemia is selected from the group consisting of hemolytic anemia, microangiopathic hemolytic anemia, hypersplenism, dyserythropoietic anemia, spherocytosis, sideroblastic anemia, autoimmune hemolytic anemia, sickle cell anemia, thalassemia, Glucose-6-phosphate dehydrogenase (G6PD)-deficient anemia, pernicious anemia, aplastic anemia, anemia caused by liver disease or renal disease, and anemia caused by the deficiency of one or more vitamins or nutrients. Some embodiments provide a method of treatment where anemia is caused by deficiency of one or more nutrients or vitamins, for example, a vitamin B12, B2, B6, C, Al, D, E or K, iron, folic acid, zinc, copper, calcium or protein.

Some embodiments provide methods for treating thrombocytopenia comprising the step of administering a therapeutically effective amount of a compound selected from Compounds 1-6 to a subject in need thereof. In some embodiments, thrombocytopenia is selected from idiopathic thrombocytopenia, alcohol-induced thrombocytopenia, drug-induced immune thrombocytopenia, thrombotic thrombocytopenic purpura, transfusion-induced thrombocytopenia, primary thrombocythemia, disseminated intravascular coagulation, hypersplenism, hemolytic uremic syndrome, paroxysmal nocturnal hemoglobinuria and immune thrombocytopenia. In some embodiments, thrombocytopenia is due to low production of platelets in bone marrow, while in some embodiments, it is due to increased breakdown of platelets in the bloodstream, spleen or liver, or due to hemodilution.

Some embodiments provide methods for treating neutropenia comprising the step of administering a therapeutically effective amount of a compound selected from Compounds 1-6 to a subject in need thereof. In some embodiments, neutropenia is selected from primary neutropenia, acute neutropenia, severe chronic neutropenia, severe congenital neutropenia (Kostmann's syndrome), severe infantile genetic agranulocytosis, benign neutropenia, cyclic neutropenia, chronic idiopathic neutropenia, secondary neutropenia, syndrome associated neutropenia, and immune-mediated neutropenia.

Some embodiments provide methods for treating neutropenia comprising the step of administering a therapeutically effective amount of a compound selected from Compounds 1-6 to a subject in need thereof, wherein neutropenia is caused or associated with radiation, alcoholism, allergic disorders, aplastic anemia, autoimmune disease, myelodysplasia, myelofibrosis, dysgammaglobulinemia, paroxysmal nocturnal hemoglobinuria, vitamin B12 deficiency, folate deficiency, viral infection, bacterial infection, spleen disorder, hemodialysis or transplantation, myeloma, lymphoma, metastatic solid tumors which infiltrate and replace the bone marrow, toxins, bone marrow failure, Schwachman-Diamond syndrome, cartilage-hair hypoplasia, dyskeratosis congenita, glycogen storage disease type IB, splenomegaly, or intrinsic defects in myeloid cells.

Some embodiments provide methods for treating leukopenia comprising the step of administering a therapeutically effective amount of a compound selected from Compounds 1-6 to a subject in need thereof. In some embodiments, leukopenia is caused or associated with one or more diseases or disorders selected from aplastic anemia, autoimmune diseases, chemotherapy, radiation, hyperthyroidism, rheumatoid arthritis, liver disorders, spleen disorders, congenital disorders, viral infections, bacterial infections and parasitic infections. In some embodiments, leukopenia is caused or associated with parasitic infection, for example, infection selected from *Acanthamoeba* keratitism, amoebiasis, ascariasis, babesiosis, balantidiasis, baylisascariasis, Chagas disease, clonorchiasis, *cochliomyia*, cryptosporidiosis, diphyllobothriasis, dracunculiasis, echinococcosis, elephantiasis, enterobiasis, fascioliasis, fasciolopsiasis, filariasis, giardiasis, gnathostomiasis, hymenolepiasis, isosporiasis, Katayama fever, leishmaniasis, Lyme disease, malaria, metagonimiasis, myiasis, onchocerciasis, pediculosis, scabies, schistosomiasis, sleeping sickness, strongyloidiasis, taeniasis, toxocariasis, toxoplasmosis, trichinosis, and trichuriasis. In some embodiments, leukopenia is caused by or associated with viral infection, for example, infection selected from HCV, HIV, influenza, Ebola virus, Marburg virus, flavivirus, Venezuelean equine encephalitis, Chikungunya virus, and West Nile virus. In some embodiments, flavivirus is selected from the group consisting of Absettarov, Alfuy, Apoi, Aroa, Bagaza, Banzi, Bouboui, Bussuquara, Cacipacore, Carey Island, Dakar bat, Dengue 1, Dengue 2, Dengue 3, Dengue 4, Edge Hill, Entebbe bat, Gadgets Gully, Hanzalova, Hypr, Ilheus, Israel turkey meningoencephalitis, Japanese encephalitis, Jugra, Jutiapa, Kadam, Karshi, Kedougou, Kokobera, Koutango, Kumlinge, Kunjin, Kyasanur Forest disease, Langat, Louping ill, Meaban, Modoc, Montana *myotis* leukoencephalitis, Murray valley encephalitis, Naranjal, Negishi, Ntaya, Omsk hemorrhagic fever, Phnom-Penh bat, Powassan, Rio Bravo, Rocio, royal farm, Russian spring-summer encephalitis, Saboya, St. Louis encephalitis, Sal Vieja, San Perlita, Saumarez Reef, Sepik, Sokuluk, Spondweni, Stratford, Tembusu, Tyuleniy, Uganda S, Usutu, Wesselsbron, west Nile, Yaounde, yellow fever, and Zika. In some embodiments, leukopenia is caused or associated with bacterial infection, for example, infection resulting from Acidobacteria, Actinobacteria, Aquificae, Bacteroidetes, Caldiserica, Chlamydiae, Chlorobi, Chloroflexi, Chrysiogenetes, Cyanobacteria, Deferribacteres, Deinococcus-*Thermus*, Dictyoglomi, Elusimicrobia, Fibrobacteres, Firmicutes, Fusobacteria, Gemmatimonadetes, Lentisphaerae, Nitrospira, Planctomycetes, Proteobacteria, Spirochaetes, Synergistetes, Tenericutes, Firmicutes, Thermodesulfobacteria, Thermomicrobia, Thermotogae, or Verrucomicrobia.

Some embodiments provide methods for treating a disease or condition selected from the group consisting of an inflammatory disorder, an allergic disorder, an autoimmune disease, and a cancer in a subject in need thereof, the method comprising administering to the human in need thereof a therapeutically effective amount of a compound selected from Compounds 1-6, or a pharmaceutically acceptable salt, ester or derivative thereof, wherein said subject is additionally undergoing proton pump inhibitor therapy; and, wherein said compound selected from Compounds 1-6 is administered at an increased daily dosage compared to the daily dosage recommended for a subject not undergoing proton pump inhibitor therapy. In some embodiments, proton pump inhibitor is selected selected from omeprazole, hydroxyomeprazole, esomeprazole, tenatoprazole, lansoprazole, pantoprazole, rabeprazole, dontoprazole, habeprazole, perprazole, ransoprazole, pariprazole, leminoprazole, tenatoprazole, S-tenatoprazole-Na, and dexlansoprazole. For example, a patient undergoing proton pump therapy is administered a daily dosage of a compound selected from Compounds 1-6 that is increased by between 25-75% of the recommended daily dosage. In one embodiment, the daily dosage of compound 1 is increased by about 200%, 100%, 75%, 70%, 65%, 60%, 55%, 50%, 45%, 40%, 35%, 30% or 25%. For example, a daily dosage of recommendation of about 800 mg of compound-1 can be increased by about 200%, 100%, 75%, 70%, 65%, 60%, 55%, 50%, 45%, 40%, 35%, 30% or 25% for patient undergoing proton pump inhibitor therapy. For example, the increased dosage can be about 2400 mg or 1600 mg or 1400 mg or about 1360 mg or about 1320 mg or about 1280 mg or about 1240 mg or about 1200 mg or about 1160 mg or about 1140 mg or about 1100 mg or about 1060 mg or about 1020 mg or about 980 mg or about 940 mg or about 900 mg. In one embodiment, the application provides methods for treating a proliferative disease or disorder in a subject in need thereof, comprising the step of administering a therapeutically effective amount of a compound selected from Compounds 1-6, or a pharmaceutically acceptable salt thereof, to said subject, wherein said subject has one or more abnormal core-binding karyotypes selected from t(8;21)(q22;q22), inv(16)(p13.1q22) and t(16;16)(p13.1;q22); or wherein said subject has one or more chromosomal abnormalities selected from the deletion of 5, 5q, 7, 7q, 17p, inv(3)(q21;q26) and t(3;3)(q21;q26); or wherein said subject has a 11q23 rearrangement of MLL gene.

Cytogenetic data help stratify patients in terms of diagnosis and evaluating prognosis for survival and risk of transformation to AML (U.S. Patent Publication No. 20100009364; Hofmann, W. K., et al., Myelodysplastic syndrome. *Annual Review of Medicine*. 2005, vol. 56, pp. 1-16). Characteristic chromosomal deletions involve chromosome 5 [del(5q), −5], chromosome 11 [del(11q)], chromosome 12 [del(12q)], chromosome 20 [del(20q)], chromosome 7 [del(7q), −7], chromosome 17 [del(17p)], and chromosome 13 [del(13q)]. Other frequent structural and/or numerical chromosomal aberrations include trisomy 8, trisomy 21, and inversion 3(q21q26). Rare reciprocal translocations include t(1; 7)(q10; p10), t(1; 3)(p36; q21), t(3; 3)(q21; q26), t(6; 9)(p23; q34), and t(5; 12)-fusion between PDGFRβ and TEL(ETV-6), (q33; p13); t(5; 7)(q33; 11.2). Some embodiments provide methods for treating proliferative diseases including AML and MDS by the administration of a compound selected from Compounds 1-6 or a pharmaceutically acceptable salt thereof to a subject in need thereof.

Some embodiments provide methods for treating a proliferative disease or disorder in a subject in need thereof, comprising the step of administering a therapeutically effective amount of a compound selected from Compounds 1-6, or a pharmaceutically acceptable salt thereof, to said subject, wherein said subject has or expresses a mixed lineage leukemia (MLL) fusion protein, a BCR-ABL fusion protein, FLT3 internal tandem duplications, a deleted or mutated p53, high or elevated levels of meningioma 1, and/or high or levels of lactate dehydrogenase.

Homeobox (HOX) proteins are homeo-domain DNA binding transcription factors that play an important role in regulation of hematopoiesis (Sitwala, *Int. J. Clin. Exp. Pathol.* 2008, March 30; 1(6):461-74). Myeloid Ecotropic Viral Integration Site 1 (MEIS1) is a co-factor of Homeobox A9 (HOXA9) that recruits additional DNA binding proteins to HOXA9 binding sites in order to maintain the Mixed Lineage Leukemia (MLL) stem cell transcriptional program (Collins, *Curr. Opin. Hematol.* 2016, July; 23(4):354-61). Over expression of these two proteins in hematopoietic stem cells (HSCs) results in a rapid and fatal leukemia when transduced HSCs are transplanted in mice (Thorsteinsdottir, *EMBO J.* 2001, February 1; 20(3):350-61). A subset of acute lymphoid leukemia (ALL), acute myeloid leukemia (AML), pro-B-acute lymphocytic leukemia (pro-B ALL), myelodysplastic syndrome (MDS) and T-cell acute lymphoblastic leukaemia (T-ALL) patients can be characterized by tumor cells collected from bone marrow showing high co-expression of HOXA9 and MEIS1 that may be associated with increased SYK protein levels. Increased SYK protein expression can be measured by evaluating pSYK levels. Some embodiments provide a method for treating patients with ALL, pro-B ALL, AML, MDS and T-ALL, where HOXA9 and MEIS1 are overexpressed, by the administration of a therapeutically effective amount of a SYK inhibitor selected from Compounds 1-6, or a pharmaceutically acceptable salt, ester or derivative thereof.

Some embodiments provide methods for treating a proliferative disease or disorder in a subject in need thereof, comprising the step of administering a therapeutically effective amount of a compound selected from Compounds 1-6, or a pharmaceutically acceptable salt thereof, to said subject, wherein said subject is administered one or more anti-cancer agents selected from the group consisting of AMG-330, anti-miR155, AntiJL-1+, CD117-MTX aptamer, CD47mAb, CD-98mAb, GO-203c, hBF4-mAb, LAIR1-mAb, IL-IRAP-mAb, MG006, miR-150, MRX-6313, MSK-777, SP-2065, SPM-2, SIRPαFc, TTT-3002, MLL/Menin inhibitor, AML-IL2/CD80, 4G8SDIEM, AG-221, AG-120, AKN-028, ALT 801, Anti-CD44 mAb, ASP-2215, AT-109, AT-406, AT-9283, AZ-1208, BGB-324, BI 836858, BMS-936564, BP-100-01, Carbozatinib, CB-839, CART-CD123, CART-CD33, CPI-613, CPI-0610, CSL-362, CWP-232291, Dacogen, Dinacilib, DC/AML fusion, Elesclomol, EPZ-5676, GSK2879552, IGN 523, INNO-305, Iomab-B, KX-2391, LeY, LOR-253, MK-8242, MGD006, Oxi-4503, PF-449913, Plerixafor, PRI-724, Rebistanib, Rigosertib, RO-5503781, PF-04449913, SG-2000, SL-401, SGN-CD33a, TCN-P, Tiecycline, Triciribine, Vismodegib, Zosuquidar, Actimab-A, AEG 35156, Belinostat, B1811283, Bismab-A, Birinapant, BL-8040, CC-486, CNDO-109, Crenolanib, Deformolus, DFP-10917, Flavopiridol, GVAX, KB-004, KPT-330, Lestartinib, Lirilumab, LO-02040, LY209314, MK8776, Omacetaxine, Pacritinib, Panobinostat, PD-616, Pdilizumab, PR-104, Pracinostat, PLX-3397, R-115777, Ribovarin, Selumetinib, SGI-110, Sorafenib, Tresosulfan, Temodar, Tosedostat, Vorinostat, WT-1, Arsenix trioxide, Clofarabine, Decitabine, Laromustine, Tipfarnib and Mylotarg.

Some embodiments provide methods of treatment for anemia, thrombocytopenia, leukopenia or neutropenia wherein said patient is not undergoing chemotherapy. For example, the subject is treated with a compound selected from Compounds 1-6 while the subject is not undergoing chemotherapy with agents such as DNA damaging agents, antibiotic agents, antimitotic agents, steroids or glucocorticoids. DNA alkylating agents can be selected from, for example, actinomycin, amsacrine, busulfan, carboplatin, chlorambucil, cisplatin, cyclophosphamide, Cytoxan, dactinomycin, daunorubicin, doxorubicin, epirubicin, iphosphamide, melphalan, merchlorethamine, mitomycin, mitoxantrone, nitrosourea, procarbazine, Taxol, Taxotere, teniposide, etoposide and triethylenethiophosphoramide. The antibiotic chemotherapy agents can be selected from dactinomycin (actinomycin D), daunorubicin, doxorubicin (adriamycin), idarubicin, anthracyclines, mitoxantrone, bleomycins, plicamycin (mithramycin) and mitomycin. The antimitotic agents can be selected from *vinca* alkaloids, a taxane, nocodazole, epothilones, navelbine and epidipodophyllotoxin. *Vinca* alkaloids can be selected from vinblastine and vincristine, or derivatives thereof. Taxanes can be selected from paclitaxel and docetaxel, or derivatives thereof.

Pharmaceutical Compositions and Modes of Administration

Compounds provided herein are usually administered in the form of pharmaceutical compositions. Thus, provided herein are also pharmaceutical compositions that contain one or more of the compounds of any of the formulae disclosed herein or a pharmaceutically acceptable salt, isomer, prodrug, or solvate thereof, and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant. In some embodiments, the pharmaceutical composition is administered orally.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound of any of the formulae described herein or a pharmaceutically acceptable salt, prodrug, or solvate thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders. In certain embodiments, the pharmaceutical composition is in the form of tablets.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound of any of the formulae described herein or a pharmaceutically acceptable salt, isomer, prodrug, or solvate thereof, can be formulated so as to provide quick, sustained or delayed release of the active ingredient after administration to the subject by employing procedures known in the art. Controlled release drug delivery systems for oral administration include osmotic pump systems and dissolution systems containing polymer-coated reservoirs or drug-polymer matrix formulations. Examples of controlled release systems are given in U.S. Pat. Nos. 3,845,770, 4,326,525, 4,902,514 and 5,616,345. Another formulation for use in the methods of the present application employs transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound of any of the above formulae or a pharmaceutically acceptable salt, prodrug, or solvate thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Dosing

The specific dose level of compounds described herein for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound of the formula per kilogram of the subject's body weight (mg/kg). Dosages of between about 0.01 and 200 mg/kg may be appropriate. In some embodiments, about 0.01 and 150 mg/kg may be appropriate. In other embodiments a dosage of between 0.05 and 100 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound of the formulae administered per dose or per day. Daily dosage of a compound may be between about 1 mg and 2,000 mg, between about 1,000 to 2,000 mg/day, between about 1 to 1,000 mg/day, between about 1 to 500 mg/day, between about 100 to 150 mg/day, between about 1 to 100 mg/day, between about 1 to 50 mg/day, between about 50 to 100 mg/day, between about 100 to 125 mg/day, between about 100 to 150 mg/day, between about 100 to 175 mg/day, between about 100 to 200 mg/day, between about 100 to 225 mg/day, between about 100 to 250 mg/day, between about 100 to 350 mg/day, between about 100 to 400 mg/day, between about 100 to 450 mg/day, or between about 100 to 500 mg/day.

When administered orally, the total daily dosage for a human subject may be between 1 mg and 1,000 mg/day, between about 1 to 100 mg/day, between about 1 to 50 mg/day, between about 50 to 100 mg/day, between 50 to 300 mg/day, between 50 to 200 mg/day, between 75 to 200 mg/day, between 75 to 150 mg/day, between 100 to 200 mg/day, between about 200 to 300 mg/day, between about 300 to 400 mg/day, between about 400 to 500 mg/day, between about 100 to 150 mg/day, between about 150 to 200 mg/day, between about 200 to 250 mg/day, between about 75 to 150 mg/day, or between about 150 to 300 mg/day.

The compounds of the present application or the compositions thereof may be administered once, twice, three, or four times daily, using any suitable mode described above.

Example

Methods: In this phase 1b/2 study (NCT02343939), patients age 18 to 70 years with previously untreated AML, preserved organ function, and ECOG≤2 were eligible to receive dose escalated entospletinib (ENTO or Compound-1) for 14 days as monotherapy (days −14 to 0) followed by combination with daunorubicin 60 mg/m2/d, cycle 1 day 1 to 3, and cytarabine 100 mg/m2/d, cycle 1 day 1 to 7. All patients received entospletinib (ENTO or Compound-1) monotherapy for up to 14 days prior to starting induction. Chemotherapy could be initiated after 5 days of monotherapy (and entospletinib continued for 4+ weeks) in patients with leukemia-related complications necessitating chemotherapy. Patients enrolled to dose level (DL) 0 and DL 1 received entospletinib 200 mg po BID and 400 mg po BID, respectively. Patients with residual disease two weeks after chemotherapy received a second induction cycle identical to the first. Entospletinib was continued without interruption until remission was assessed at count recovery.

Results: Twelve patients enrolled with a median age of 54 (range, 18-69) years. Patients were in the following European LeukemiaNet genetic risk groups: favorable (n=1), intermediate I (n=3), intermediate II (n=2), and adverse (n=4), respectively. Three patients were not evaluable for dose limiting toxicity (DLT) assessment and were replaced (due to detection of CNS disease requiring non-study therapy (n=1), and withdrawal of consent unrelated to drug toxicity (n=2)). Single-agent entospletinib during the window period was well tolerated; toxicities after combination with intensive chemotherapy were common and typical. Among three patients treated at 200 mg BID, no DLT was observed. Of three patients treated at 400 mg BID, a patient with documented fungal pneumonia developed grade 3 pneumonitis that was possibly related to entospletinib. Although this did not meet DLT criteria, DL 1 was expanded with 3 additional patients, none of whom experienced DLT. Overall, the most common non hematologic adverse events (inclusive of intensive chemotherapy periods) were febrile neutropenia, nausea, and diarrhea. Based on this clinical experience and compiled pharmacokinetic data demonstrating lack of benefit to further dose escalation, 400 mg BID was selected as the recommended phase 2 dose. Responses were seen at both levels. Among the 3 patients treated at 200 mg BID, two required a second induction but each achieved a complete remission (CR) (3/3; 100%). Of the 6 patients treated at 400 mg BID, none required a second induction and the CR rate was also 100%. Remarkably, an 18 year old male with 11q23-rearranged AML achieved morphologic and cytogenetic CR after only the 14 day entospletinib monotherapy window (prior to chemotherapy). Another patient with 11q23-rearranged AML had significant platelet response during the window period (this patient refused disease evaluation by marrow aspiration prior to chemotherapy).

Figure 1:
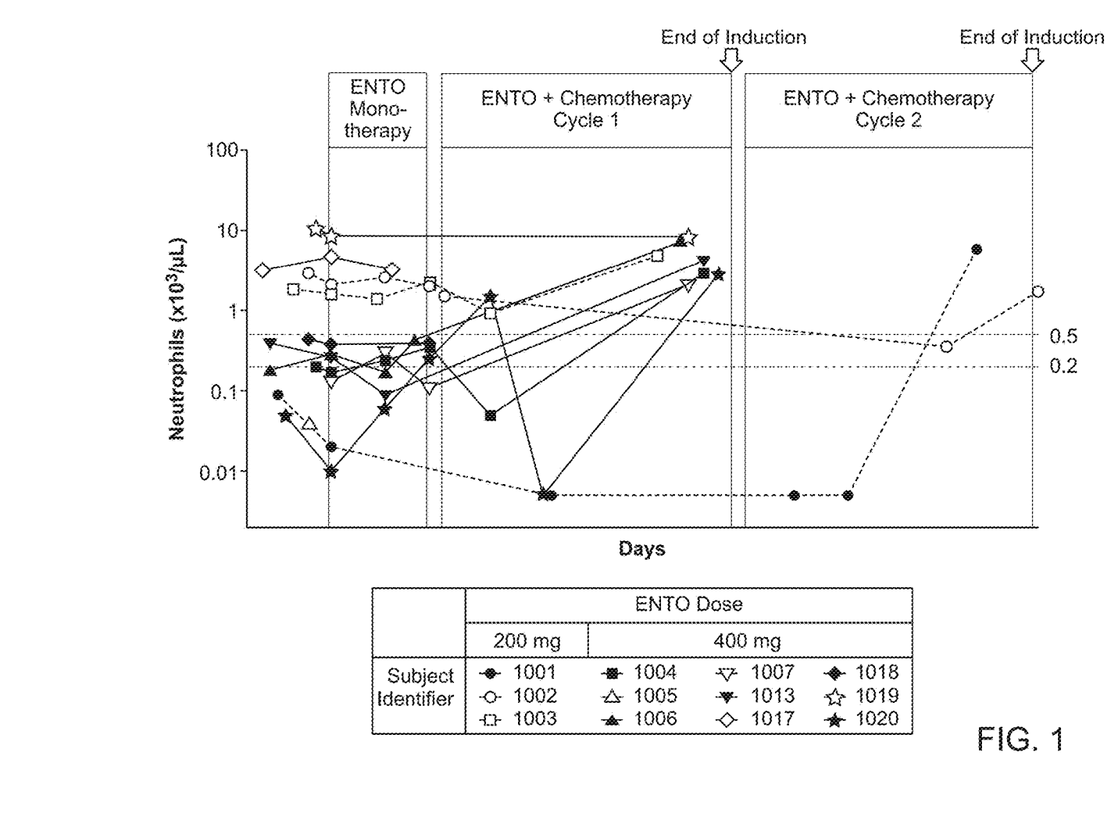
FIG. 1: Neutrophil counts in patients receiving chemotherapy and 200 or 400 mg twice daily dose of entospletinib (ENTO or Compound-1). The figure shows daily levels for individual patients and neutrophil recovery through induction treatment.

A neutrophil recovery plot for all enrolled subjects in the above study is provided in FIG. 1. During the entospletinib monotherapy lead-in period, absolute neutrophil counts (ANC) remained largely stable. All three of the evaluable subjects at the entospletinib 400 mg dose level who were under the severe neutropenia cutoff of 200/μL ANC at baseline recovered to above 200/μL during treatment. Severe neutropenia in these subjects was short lived, with a median (Q1, Q3) time to recovery of 8 (8, 14) days; individual values were 8, 8, and 14 days. The only evaluable subject with severe neutropenia at baseline at the entospletinib 200 mg dose level also recovered during treatment (recovery time of 66 days). Among the five subjects (treated at both entospletinib dose levels) who did not have severe neutropenia at baseline and had at least one post-baseline ANC assessment, none experienced severe neutropenia at any time during induction treatment; however, two of the five subjects, both treated at the entospletinib 400 mg dose level, did experience severe neutropenia during the entospletinib monotherapy lead-in period, which recovered to above 200/μL by the end of the first induction cycle in both subjects (FIG. 1).

Figure 2:
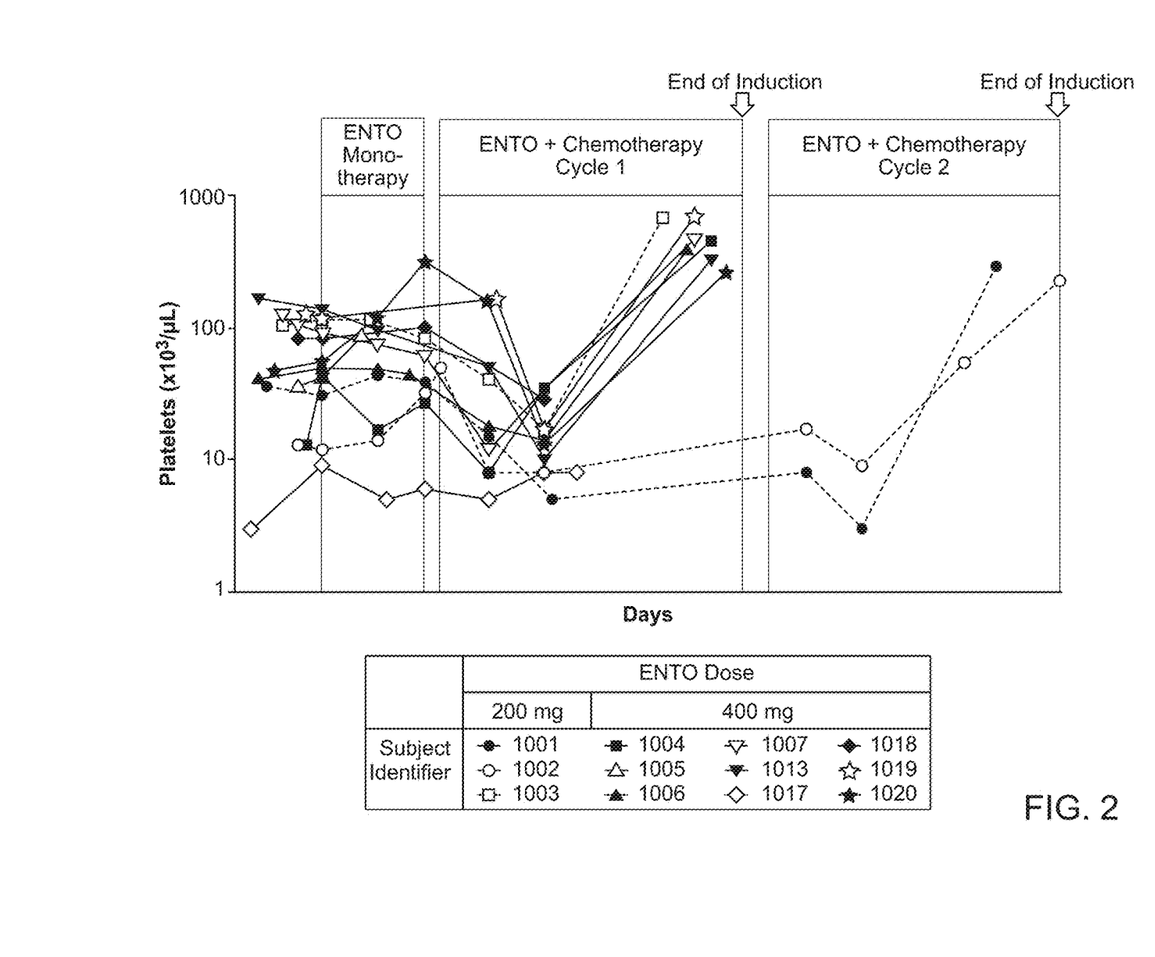
FIG. 2: Platelet counts in patients receiving chemotherapy and 200 or 400 mg doses of entospletinib (ENTO or Compound-1). The figure shows daily levels for individual patients and platelet recovery through induction treatment.
Figure 3:
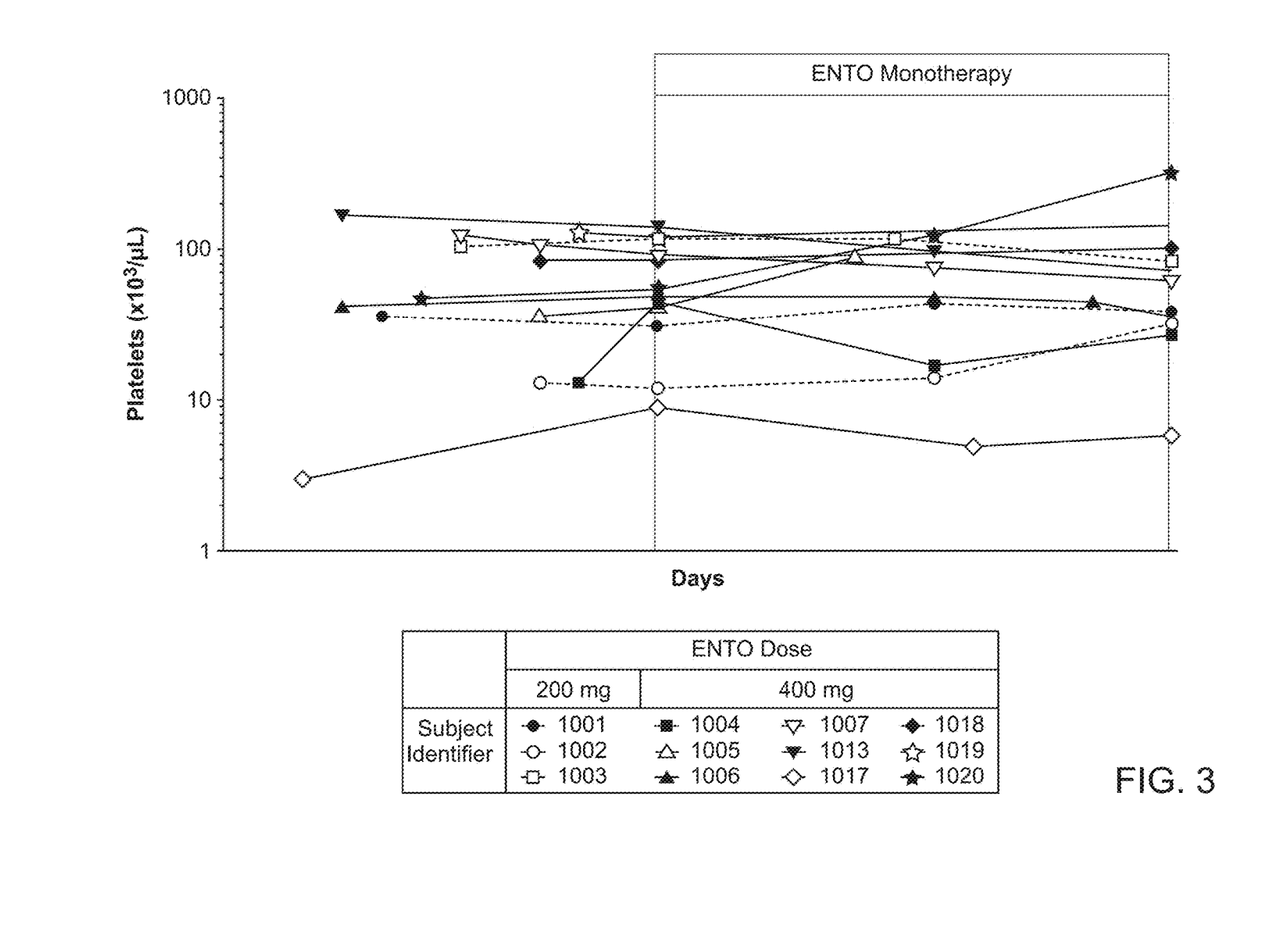
FIG. 3: Platelet recovery during the entospletinib (ENTO or Compound-1) monotherapy lead-in window.
Figure 4:
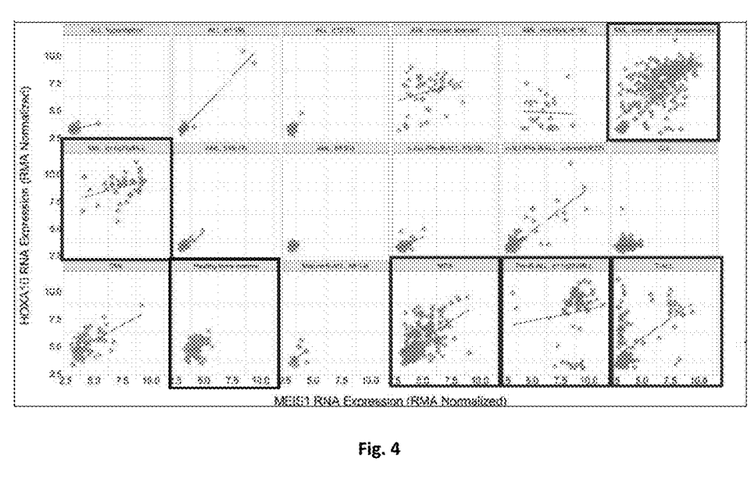
FIG. 4: Scatter Plot of MEIS1 and a HOXA10 Expression in Leukemia Subtypes. Leukemia subtypes with high co-expression of HOXA10 and MEIS1 are boxed in red. Healthy bone marrow is boxed in blue. Data source: Microarray Innovations in Leukemia (MILE) study (GSE13159, PMID: 18573112 and 20406941).
Figure 5:
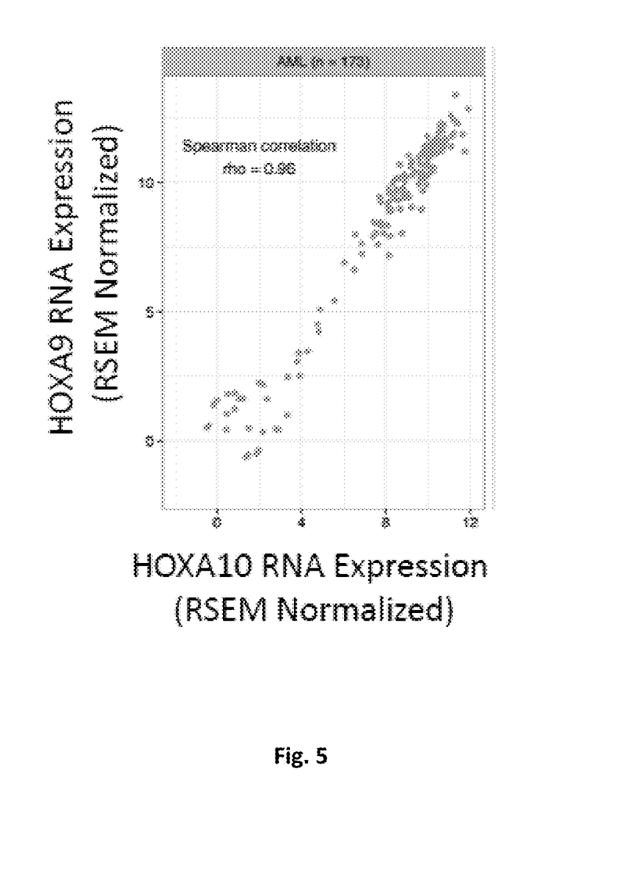
FIG. 5: HOXA10 and HOXA9 RNA Expression is Highly Correlated in AML. Data Source: The Cancer Genome Atlas (TCGA), RNAseq data, release 2016_01_28.
Figure 6:
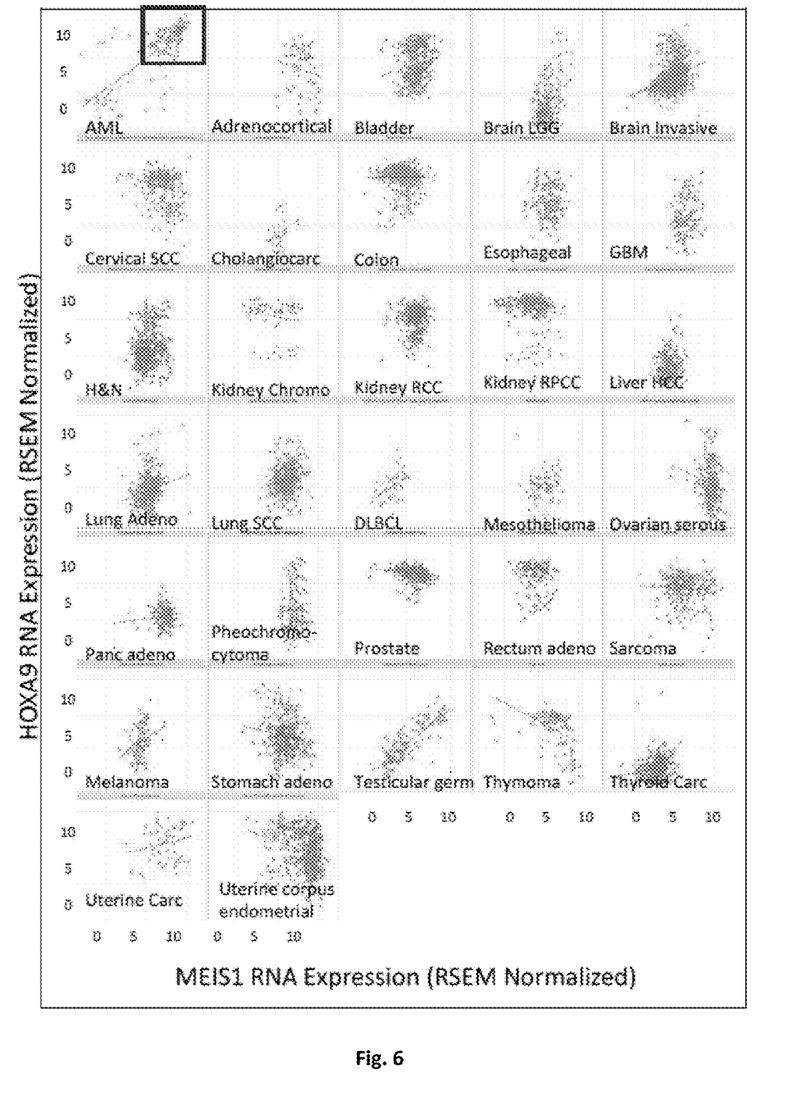
FIG. 6: Expression of HOXA9 and MEIS1 RNA in Cancer Types from TCGA. MEIS1 and HOXA9 RNA levels were plotted for cancers in the TCGA. Blue lines in each panel represent the linear regression line. The red box signifies the high HOXA9 and MEIS1 population in AML. Data Source: TCGA, RNAseq data, release 2016_01_28.
Figure 7:
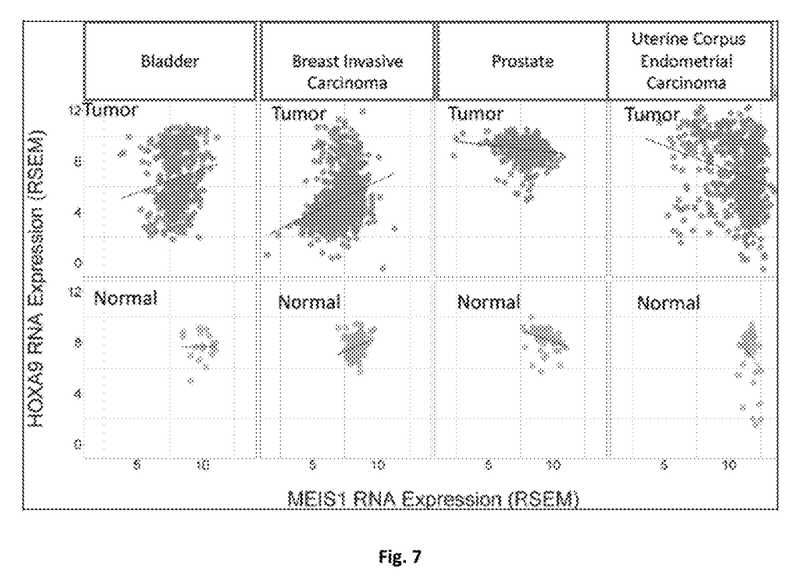
FIG. 7: Expression of HOXA9 and MEIS1 RNA in Tumor and Normal from Bladder, Breast Invasive Carcinoma, Prostate and Uterine Cancers from TCGA Data. Data Source: TCGA, RNAseq data, release 2016_01_28.

A plot of platelet counts through induction treatment for all enrolled subjects in the above study is provided in FIG. 2. During the two week entospletinib monotherapy window, platelet count remained stable, or in some cases, improved from baseline. One subject received platelet transfusions at the entospletinib 200 mg dose level and no transfusions were required at the entospletinib 400 mg dose level. During induction treatment, the mean number of transfusions required per subject was 4.1 during Cycle 1 and 5.5 during Cycle 2. Across the monotherapy lead-in and induction treatment cycles, the mean number of platelet transfusions required per subject was 8.7 at the ENTO 200 mg dose level, 4.1 at the entospletinib 400 mg dose level, and 5.5 overall (FIG. 3).

Throughout this specification, various patents, patent applications and other types of publications (e.g., journal articles) are referenced. The disclosure of all patents, patent applications, and publications cited herein are hereby incorporated by reference in their entirety for all purposes.

What is claimed is:

1. A method of treating or reducing aplastic anemia in a patient in need thereof, comprising administering to the patient an effective amount of a compound selected from:

Compound-1

Compound-2

Compound-3

Compound-4

, and

Compound-5 or a pharmaceutically acceptable salt thereof.

2. The method of claim 1, wherein compound is or a pharmaceutically acceptable salt thereof.

3. The method of claim 1, wherein compound is or a pharmaceutically acceptable salt thereof.

4. The method of claim 1, wherein compound is or a pharmaceutically acceptable salt thereof.

5. The method of claim 1, wherein compound is or a pharmaceutically acceptable salt thereof.

6. The method of claim 1, wherein compound is or a pharmaceutically acceptable salt thereof.

* * * * *